(12) United States Patent
Reiley (10) Patent No.: US 8,808,389 B2
(45) Date of Patent: *Aug. 19, 2014

(54) ANKLE REPLACEMENT SYSTEM

(71) Applicant: Inbone Technologies, Inc., Boulder, CO (US)

(72) Inventor: Mark A. Reiley, Piedmont, CA (US)

(73) Assignee: Inbone Technologies, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/936,806

(22) Filed: Jul. 8, 2013

(65) Prior Publication Data

US 2013/0297034 A1    Nov. 7, 2013

Related U.S. Application Data

(60) Continuation of application No. 13/231,507, filed on Sep. 13, 2011, now Pat. No. 8,480,755, and a continuation of application No. 12/425,041, filed on Apr. 16, 2009, now Pat. No. 8,034,115, and a division of application No. 11/037,916, filed on Jan. 18, 2005, now Pat. No. 8,048,164, and a division of application No. 10/700,283, filed on Nov. 3, 2003, now Pat. No. 6,860,902, and a division of application No. 09/694,100, filed on Oct. 20, 2000, now Pat. No. 6,663,669.

(60) Provisional application No. 60/160,892, filed on Oct. 22, 1999.

(51) Int. Cl.
*A61F 2/42* (2006.01)
(52) U.S. Cl.
USPC .................................................. 623/21.18
(58) Field of Classification Search
CPC ........................................................ A61F 2/42
USPC ...................................................... 623/21.18
See application file for complete search history.

(56) References Cited

U.S. PATENT DOCUMENTS 8,034,115 B2 * 10/2011 Reiley .................... 623/21.18

* cited by examiner

*Primary Examiner* — David Isabella
*Assistant Examiner* — Ann Schillinger
(74) *Attorney, Agent, or Firm* — Duane Morris LLP

(57) ABSTRACT

A total ankle replacement system, novel surgical method for total ankle replacement, and novel surgical tools for performing the surgical method are described. The total ankle replacement system includes the calcaneus in fixation of a lower prosthesis body, thereby significantly increasing the amount of bone available for fixation of the lower prosthesis body and allowing the lower prosthesis body to be anchored with screws. The total ankle replacement system further includes a long tibial stem which can also be anchored into the tibia with, for example, screws, nails, anchors, or some other means of attachment. The novel surgical arthroscopic method allows introduction of ankle prostheses into the ankle joint through an exposure in the tibial tubercle. Various novel surgical instruments, such as a telescoping articulating reamer and a talo-calcaneal jig, which facilitate the novel surgical method, are also described.

2 Claims, 6 Drawing Sheets

ANKLE REPLACEMENT SYSTEM

RELATED APPLICATIONS

This application is a continuation of U.S. patent application Ser. No. 13/231,507, now U.S. Pat. No. 8,480,755, filed on Sep. 13, 2011, which is a continuation of U.S. patent application Ser. No. 12/425,041, now U.S. Pat. No. 8,034,115, filed on Apr. 16, 2009, which is a divisional of U.S. patent application Ser. No. 11/037,916 filed on Jan. 18, 2005, now U.S. Pat. No. 8,048,164, which is a division of U.S. patent application Ser. No. 10/700,283, now U.S. Pat. No. 6,860,902, filed on Nov. 3, 2003, which is a divisional of U.S. patent application Ser. No. 09/694,100 filed Oct. 20, 2000, now U.S. Pat. No. 6,663,669, which claims the benefit of United States Provisional Patent Application Serial No. 60/160,892, filed Oct. 22, 1999, and entitled "Ankle Replacement Systems," all of which are incorporated herein by reference in their entireties.

BACKGROUND OF THE INVENTION

1. Field of the Invention

The invention relates to ankle replacement systems including designs, methods and apparatus that reduce and/or prevent problems associated with subsidence, loosening, and late infection, in part, by incorporating a novel surgical procedure for replacing an ankle, at least in part, through a tibial tubercle exposure. The present invention is also directed to novel surgical instruments useful for performing an ankle replacement procedure.

2. Description of the Background

Until the early to mid 1970's, patients with injured or diseased ankle joints commonly resulting from rheumatism, or degenerative or traumatic arthritis, had few options when their ankle joints failed. The most common procedure to help these patients regain some use of their ankle was obliteration of the joint by fusion, a procedure that is still commonly used today. Fusion, however, rendered the ankle stiff and generally immobile relative to the lower leg, resulting in limited use and additional stresses on the knee and hip joints.

Probably the first reported use of total ankle prosthesis was by Buckholz in 1969. The medical community recognized that such ankle replacement led to largely increased use of the ankle joint because the replacement permitted ankle ranges of motion which generally attempted to mimic the natural human joint. Since that time, ankle replacement prostheses have become increasingly common in use and improved in design.

An early ankle replacement prosthesis, disclosed in U.S. Pat. No. 3,886,599, incorporated herein by reference, consisted of an articulated two-part prosthesis having a convex-to-convex bearing surface provided by an upper metallic portion and a lower portion formed of high density polyethylene. The upper metallic portion had a stem adapted for engagement with a prepared distal end of the tibia, and the lower portion had a shank adapted for engagement with and connection to a prepared surface of the talus.

Another early ankle replacement prosthesis, disclosed in U.S. Pat. No. 4,069,518, incorporated herein by reference, comprised a talar member with three adjacent longitudinally and laterally convexly shaped bearing surfaces with a means for attaching the talar member to the talus; and a tibial member with three complementary longitudinally and laterally concavely shaped bearing surfaces with a means for attaching the tibial member to the tibia.

Although these types of ankle replacements had some initial success in helping patients regain use of their ankle joint, the long range prognosis for patients has not been good. For example, by the mid 1980's, long term follow-ups were reported for patients who had received these types of ankle replacements in the early to mid 1970's. At a follow-up of five years, failure rates were reported to be from 35% to 76% in ankle arthroplasties. Failures have been found in all models of total ankle replacement including the Mayo Clinic Total Ankle, the Oregon, and the Beck-Steffee models. See Kitaoka, H. B. et al., Clinical Results of the Mayo Total Ankle Arthroplasty, J. Bone Joint Surg. Am., 1996; see also Wynn, A. H. et al., Long-term follow-up of the Conaxial (Beck-Steffee) Total Ankle Arthroplasty, Foot Ankle, 1992. Complications included aseptic loosening, delayed wound healing, wound dehiscence, and prosthetic subsidence.

Another ankle replacement device was described in a similar time period in U.S. Pat. No. 4,232,404, incorporated herein by reference. This prosthesis comprises a talar component with a convex articulatory surface that has an intermediate part-circular-cylindrical area coaxially flanked at each end by similar mutually divergent part-conical areas. The prosthesis also has a tibial component with an asymmetrical concave articulatory surface complimentary with the convex cylindrical area and one of the conical areas of the talar component. Additionally, this device has a fibular component which has an articulatory surface engaged with the other conical areas.

A similar device with tibial, fibular, and talar members has been in use since 1984 under the name AGILITY™ Ankle by DePuy of Warsaw, Ind. In 1997, outcomes of the first 100 total ankle arthroplasties using the AGILITY™ Ankle were reported by Dr. Frank G. Alvine, who had performed all 100 surgeries between 1984 and 1993. Approximately 61% of the replacements were reported as successful syndesmosis fusions, while the remaining cases evidenced various problems from delayed unions and nonunions which were often associated with the development of ballooning and circumferential lysis at the tibial component. See Orthopaedics Today, Jul. 7, 1997, pp. 16-17. The AGILITY™ Ankle takes advantage of tibiofibular sydesmosis for increased contact and better force distribution than the previous ankle replacements that relied on stability from connections to the talus and tibia. However, the tibiofibular syndesmosis is a large contributing factor in loosening and ballooning osteolysis problems encountered with the AGILITY™ Ankle.

A more current ankle replacement device is described in U.S. Pat. No. 5,766,259, incorporated herein by reference. This prosthesis also comprises tibial, talar, and fibular components. A floating bearing is located between the tibial and talar prosthesis components. The floating bearing makes full contact with the talar component and is capable of limited medial-lateral and fore and aft movement with the tibial component. The fibular component has a plastic insert which cooperates with the talar and tibial components to provide stability to the ankle joint.

A common element between the previous ankle replacement systems, the AGILITY™ Ankle and the system described in U.S. Pat. No. 5,766,259 is that they all comprise a talar member, fixed to the talus, as one of their main functioning components. The talus, however, is relatively small, providing a small area of bone for fixation. Also, in most of these ankle replacement systems, the talar component is cemented to the talus. The combination of fixation with bone cement to a small fixation area allows for erosion of the cement from the fixation area and an increase in compliance due to formation of a soft tissue capsule over time. This contributes to aseptic loosening and migration of the device. Furthermore, although more recent replacements have attempted to alleviate stress from the tibia and talus by incorporating a fibular component and infusing tibiofibular syndesmosis, they still face common problems of prosthesis migration and loosening, and osteolysis at the tibial component.

Another common element between these previous systems is that they are installed through incisions made at or near the ankle Such surgical procedures require making large incisions at the ankle, moving the tendons and other soft tissue aside, and separating the tibia and fibula from the talus— essentially detaching the foot from the leg—to install the device, subsequently requiring complicated realignment and reattachment of the foot. In addition, these devices typically incorporate a relatively short tibial component to simplify installation. These procedures commonly result in infection and extended healing time with possible replacement failure from improper realignment. The surgery also has increased risks associated with cutting or damaging neighboring nerves and tendons which may lead to further complications.

There is, therefore, a need in the field for a total ankle replacement system that reduces the occurrence of subsidence and aseptic loosening while retaining the majority of the foot's natural motion. There is also a need for a less invasive surgical method to install such a device to provide improved healing and a decreased failure rate.

SUMMARY OF THE INVENTION

The present invention overcomes the problems and disadvantages associated with current strategies and systems in total ankle replacement (TAR). In particular, the present inventive ankle replacement method and system is designed to prevent subsidence and aseptic loosening, problems common to the TAR devices currently in use. This device allows fixation of the lower prosthesis body to the calcaneus and/or the talus, thereby significantly increasing the bone available for fixation. The enlarged available bone base allows fixation of larger trays and prosthetic bases and allows for anchoring of the lower prosthesis body with screws or other fixation methods not possible with fixation to only the talus. This prosthesis system provides greater stability and stress absorption for the prosthetic ankle joint, and decreases the probability of prosthesis loosening and subsidence.

In one embodiment, the novel ankle replacement prosthesis comprises a member that is attached to the calcaneus. In another embodiment, the novel ankle replacement prosthesis comprises a lower member which is attached to both the talus and calcaneus in such a way as to fuse the talus to the calcaneus. In yet another embodiment, the novel ankle replacement prosthesis comprises a lower member that is attached to both the talus and the calcaneus, but which allows some relative movement between the talus and calcaneus, thereby closely mimicking the natural movement of the human foot. Said lower member could comprise a stem which incorporates a joint allowing relative movement between the talus and the calcaneus in a side-to-side manner. In a further embodiment, the lower member comprises a bony in-growth stem. The bony in-growth stem may be about 45 to 75 mm in length and 7 to 15 mm wide and may be installed in a preformed cavity in the bone that exists from the top of the talus to the distal calcaneus. In yet another embodiment, the bony in-growth stem is secured into the bone, for example, by screws, nails, anchors, or some other means of attachment.

In a further, embodiment, the novel ankle replacement system comprises an upper prosthesis body. The upper prosthesis body comprises a tibial prosthesis which further comprises a long stem, approximately 150 mm in length, preferably made of metal. In one embodiment, the long metal stem is covered with bony in-growth scintering.

The present invention also relates a novel surgical procedure for performing TAR which reduces healing time and probability of infection, problems which contribute to the failure rate of currently available TAR systems. The novel surgical procedure comprises introducing ankle prostheses for TAR through the tibia into the ankle. In one embodiment, an exposure is made at the tibial tubercle with an awl. The tibia and tibial plafond are reamed with a tibial reamer inserted through the tibial tubercle exposure. Bony cuts are made in the talus and the end of the tibia. A hole is drilled from the talus into the posterior section of the calcaneus using a talar stem jig. After cartilage has been scraped from the talocalcaneal joint, a talo-calcaneal bony ingrowth metal stem is installed into the drill hole. A talar tray and a plastic dome are placed over the Morse taper on the talo-calcaneal stem and the talar tray is fixed to the talus and calcaneus. A concave tibial dome is placed in the ankle joint. A tibial stem is passed down the tibia to the ankle joint. The end of the tibial stem is locked into the tibial component and the stem is fixed into the tibia with, for example, screws. As part of this procedure, if desired, additional incisions may be made in the foot and/or ankle to allow access to the joint and/or bones of the foot.

In a further embodiment, the top of the talus and end of the tibia may be reamed with a reamer fitted over the end of a rotating shaft which passes through the tibia instead of, or in addition to, cutting the bone. In another embodiment, the metal talar tray may be fixed to the talus and calcaneus with screws. In yet another embodiment, the tibial stem may be fixed to the tibia with screws.

Other objects, advantages, and embodiments of the invention are set forth in part in the description which follows, and in part, will be obvious from this description, or may be learned from the practice of the invention.

DESCRIPTION OF THE INVENTION

System

As embodied and broadly described herein, the present invention is directed to a novel system and method for Total Ankle Replacement (TAR). The ankle replacement system of the present invention includes a lower prosthesis body desirably fixed to the calcaneus and/or the talus, which greatly increases the amount of bone available for fixation as compared with conventional TAR systems, which traditionally included only the talus in fixation of a lower prosthesis. The enlarged available bone base allows fixation of larger talar trays or other prosthetic bases to provide greater prosthesis stability, and allows for anchoring of the lower prosthesis body with, for example, screws. This design provides greater stability and stress absorption for the prosthetic ankle joint, and decreases the probability of prosthesis loosening and subsidence.

Figure 1:
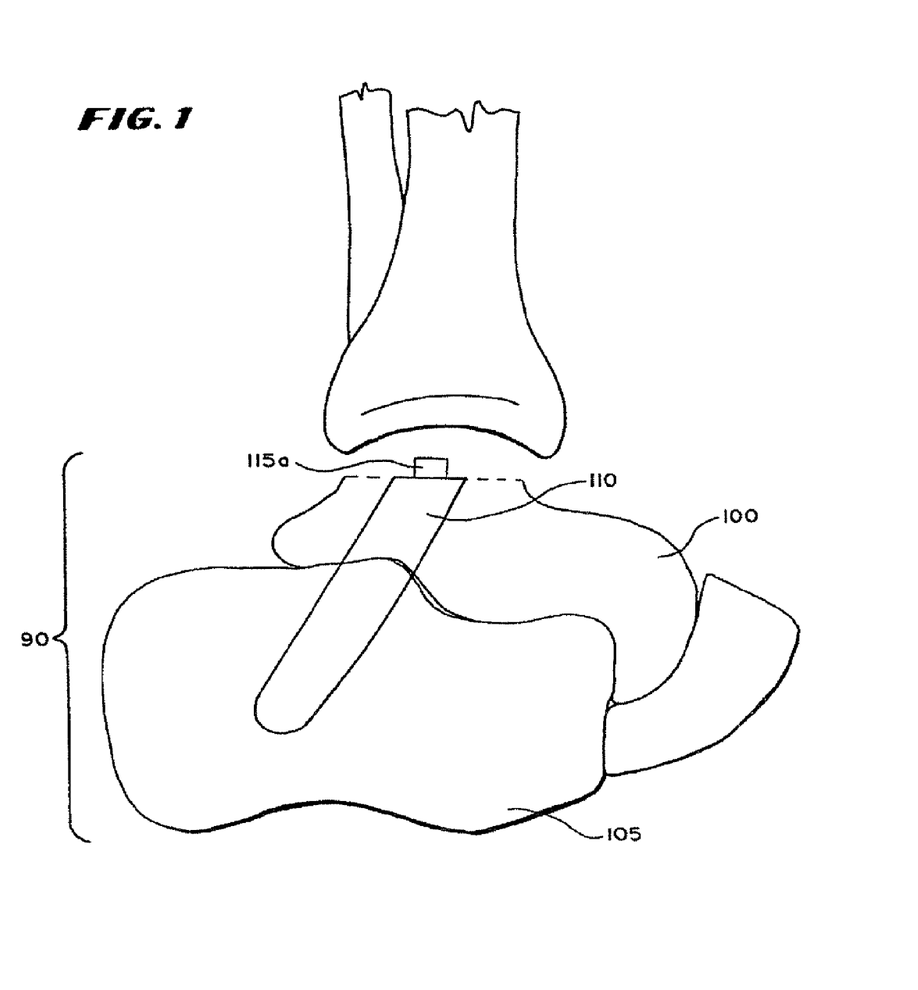
FIG. 1 is a lateral view of the subtalar joint depicting talo-calcaneal stem which has been installed into a preformed cavity in the talus and calcaneus.
Figure 2:
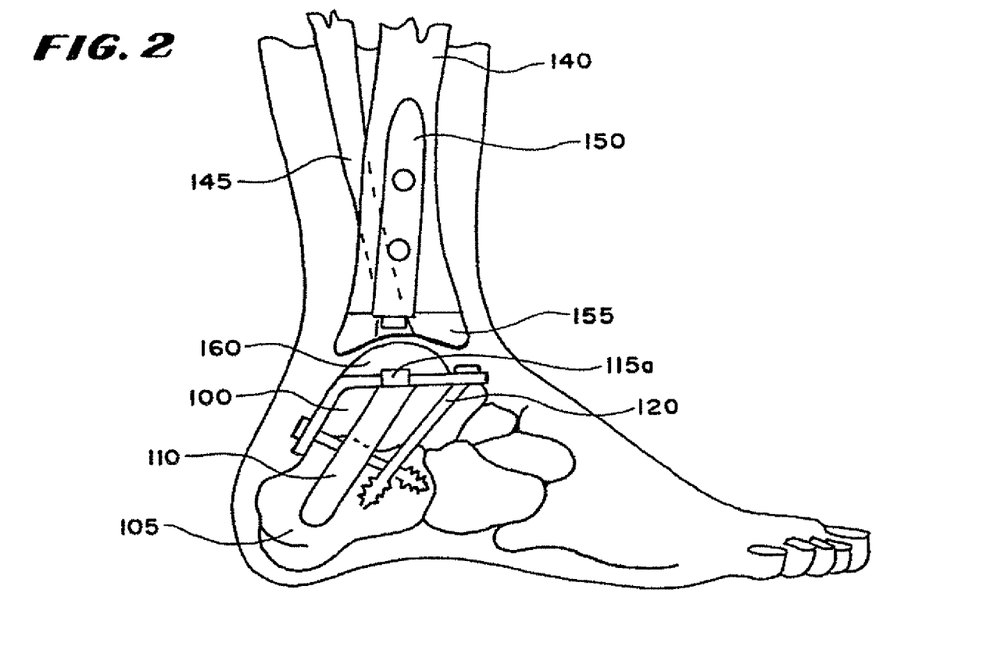
FIG. 2 is a lateral view of the foot and ankle depicting one embodiment of a TAR system of the present invention.

In one embodiment of the present invention, the subtalar joint is fused to allow fixation of the lower prosthesis body to both the talus and calcaneus. The subtalar joint may be fused using any method common to those of skill in the surgical arts including, but not limited to, fusion with poly (methylmethacrylate) bone cement, hydroxyapatite, a ground bone and marrow composition, plates and screws, or a combination thereof. In the preferred embodiment, as depicted in FIG. 1 and FIG. 2, the talus and calcaneus are fused together with a talo-calcaneal stem 110.

The talo-calcaneal stem 110 may be made of various materials commonly used in the prosthetic arts including, but not limited to, titanium, titanium alloys, tantalum, chrome cobalt, surgical steel, or any other total joint replacement metal and/or ceramic, bony ingrowth surface, sintered glass, artificial bone, any uncemented metal or ceramic surface, or a combination thereof. The talo-calcaneal stem may further be covered with various coatings such as antimicrobial, antithrombotic, and osteoinductive agents, or a combination thereof. These agents may further be carried in a biodegradable carrier material with which the pores of the surface of the talo-calcaneal stem 110 may be impregnated. See U.S. Pat. No. 5,947,893, which is incorporated herein by reference. If desired, the talo-calcaneal stem may be coated and/or formed from a material allowing bony ingrowth, such as a porous mesh, hydroxyapetite, or other porous surface.

The talo-calcaneal stem 110 may be any size or shape deemed appropriate to fuse the subtalar joint 90 of a patient and is desirably selected by the physician taking into account the morphology and geometry of the site to be treated. The physician is desirably able to select the desired size and/or shape based upon prior analysis of the morphology of the target bone(s) using, for example, plain film x-ray, fluoroscopic x-ray, or MRI or CT scanning. The size and/or shape is selected to optimize support and/or bonding of the stem to the surrounding bone(s). The stem 110 may be variable lengths from 2 cm to 12 cm and variable widths from 4 to 14 mm. In the preferred embodiment, the talo-calcaneal stem 110 is approximately 65 to 75 mm in length and approximately 7 to 10 mm wide. While in the disclosed embodiment the stem has a circular cross-section, it should be understood that the stem could formed in various other cross-sectional geometries, including, but not limited to, elliptical, polygonal, irregular, or some combination thereof. In addition, the stem could be arced to reduce and/or prevent rotation, and could be of constant or varying cross-sectional widths.

The talo-calcaneal stem 110 is passed from the top of the talus into the distal calcaneus, preferably through a cavity that has been drilled through the talus and calcaneus for fixation of the talo-calcaneal stem 110. The talo-calcaneal stem 110 or a bone jig may be further adapted so that the talo-calcaneal stem 110 is inserted as the cavity is being drilled or so that the talo-calcaneal stem itself is used to drill the hole. Moreover, if desired the stem could incorporate screw holes or other openings to accommodate interlocking hardware, such as screws, to increase fixation and minimize rotation.

The talo-calcaneal stem 110 may additionally have interlocking components, at its top surface to allow other components of the talo-calcaneal prosthesis to lock and/or fit into the talo-calcaneal stem. In the preferred embodiment, the talo-calcaneal stem 110, has a Morse taper 115a at its upper talar end.

Figure 3:
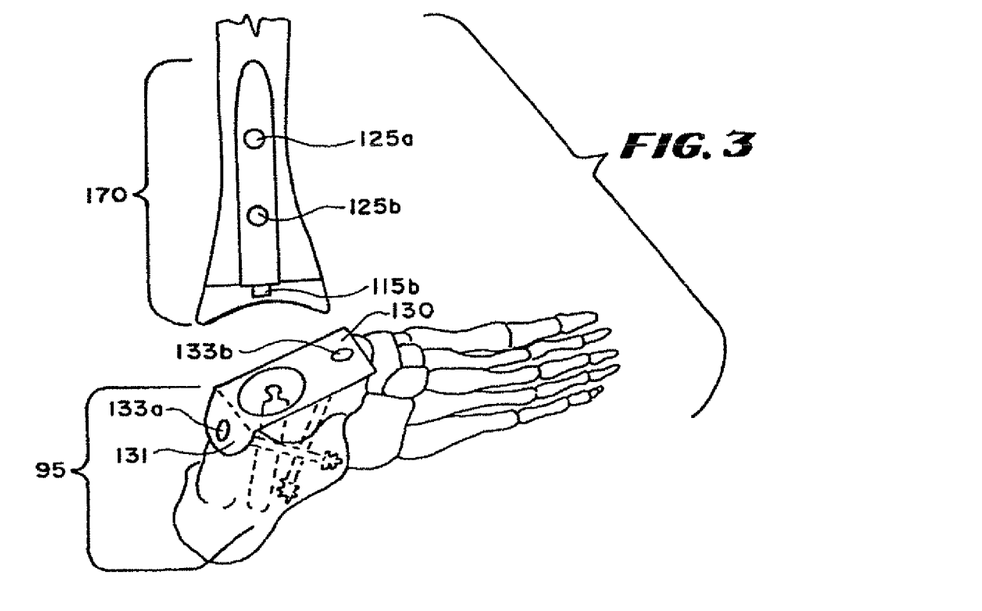
FIG. 3 is a lateral/skewed top view of the TAR system embodiment of FIG. 2.

In one embodiment, a tray 130 is fixed to the top of the talus. In another embodiment a tray, any prosthetic base, or any lower prosthesis body may be fixed or anchored to a fused subtalar joint, or to the calcaneus only, or to both the talus and calcaneus in an unfused subtalar joint. In the preferred embodiment as depicted in FIG. 2 and FIG. 3, the tray 130 has an overhang portion 131 which allows the tray 130 to overlap both the talus 100 and part of the calcaneus 105. The tray 130 and overhang portion 131 may be made of various materials commonly used in the prosthetic arts including, but not limited to, polyethylene, biologic type polymers, hydroxyapetite, rubber, titanium, titanium alloys, tantalum, chrome cobalt, surgical steel, or any other total joint replacement metal and/or ceramic, bony ingrowth surface, sintered glass, artificial bone, any porous metal coat, metal meshes and trabeculations, metal screens, uncemented metal or ceramic surface, other biocompatible materials, or any combination thereof.

The tray 130 and overhang portion 131 may further be covered with various coatings such as antimicrobial, antithrombogenic, and osteoinductive agents, or a combination thereof. See U.S. Pat. No. 5,866,113 to Hendriks, et al, incorporated herein by reference. These agents may further be carried in a biodegradable carrier material with which the pores of the tray 130 and overhang portion 131 may be impregnated. In one preferred embodiment, the tray comprises a metal-backed polyethylene component.

Figures 4, 5:
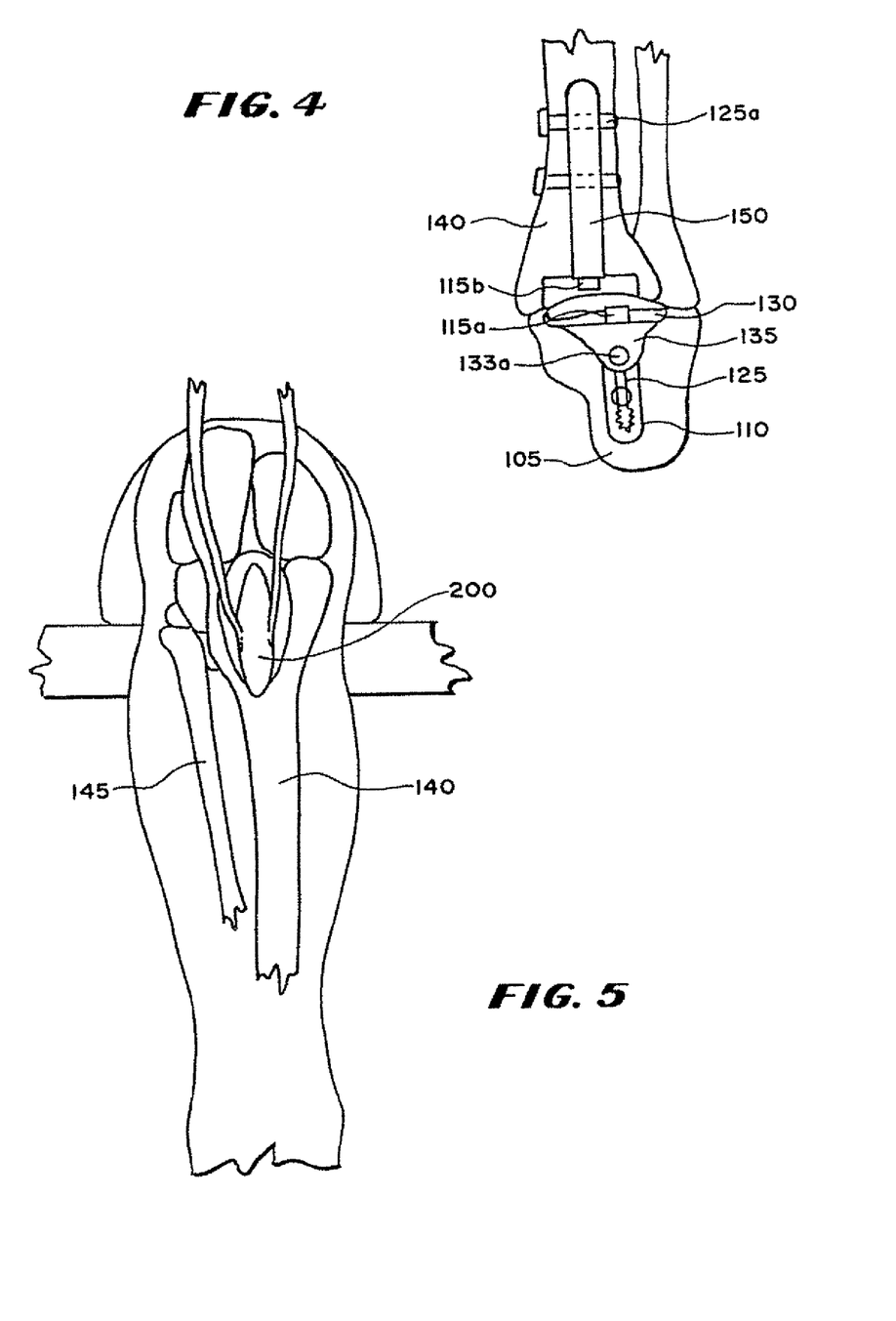
FIG. 4 is a posterior view of one embodiment of an installed TAR system of the present invention.
FIG. 5 is a view of the human leg depicting a tibial tubercle exposure.

40). The tray 130 and/or the overhang portion 131 may be fixed to the subtalar joint 90 with poly(methylmethacrylate) bone cement, hydroxyapatite, a ground bone and marrow composition, screws, or a combination thereof, or any other fixation materials common to one of skill in the art of joint replacement surgery. In the preferred embodiment, the tray 130 and overhang portion 131 are fitted over the Morse taper 115a of the talo-calcaneal stem 110 and fixed to the talus and calcaneus with screws 133a and 133b. In the preferred embodiment, as best seen in FIG. 4, screw 133a transects talo-calcaneal stem 110 to further fix and stabilize the talo-calcaneal stem 110 to the subtalar joint 90. If desired, the screws can extend anteriorly, posteriorly, medially, laterally and/or at oblique angles, or any combination thereof. Alternatively, or in combination with other fixation methods, the talo-calcaneal stem 110 may be fixed into the bone cavity with a bone cement.

A lower prosthesis body may be attached to the tray 130 and/or an interlocking device and/or directly to sections of the subtalar joint 90. In the preferred embodiment, a plastic convex dome 160, preferably made of materials such as plastic, ceramic, or metal, is attached to Morse taper 115a. In this embodiment, the lower prosthesis body 95 of the present invention comprises: a talo-calcaneal stem 110 made of any total joint material or materials commonly used in the prosthetic arts, including, but not limited to, metals, ceramics, titanium, titanium alloys, tantalum, chrome cobalt, surgical steel, or any other total joint replacement metal and/or ceramic, bony in-growth surface, sintered glass, artificial bone, any uncemented metal or ceramic surface, or a combination thereof, the stem being desirably located in a cavity formed through the talus 100 and calcaneus 105, the stem further comprising a Morse taper 115a at its upper surface; a tray 130 made of any total joint material or materials commonly used in the prosthetic arts, including, but not limited to, metals, ceramics, titanium, titanium alloys, tantalum, chrome cobalt, surgical steel, or any other total joint replacement metal and/or ceramic, bony in-growth surface, sintered glass, artificial bone, any uncemented metal or ceramic surface, or a combination thereof, with an overhang portion 131, the tray 130 and overhang portion 131 being fitted over the subtalar joint 90 and the Morse taper 115a of the bony in-growth stem 110, and fixed to the talus 100 and calcaneus 105 with two screws 133a and 133b, wherein screw 133a further transects and fixes talo-calcaneal stem 130; and a polyethylene, or other plastic, ceramic, or metal convex dome 160 which is locked into the Morse taper 115a.

Figure 8:
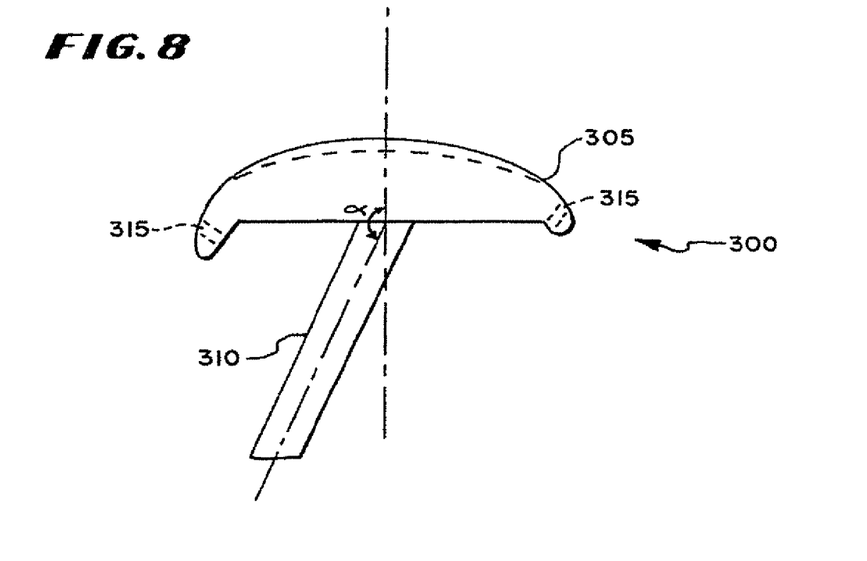
FIG. 8 is a side view of one embodiment of a lower prosthesis body constructed in accordance with the teachings of the present invention.
Figure 9:
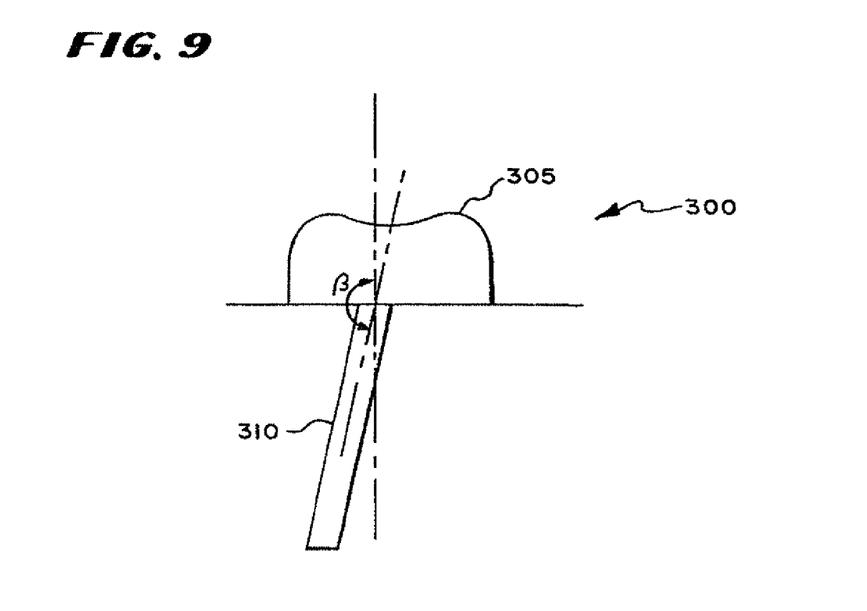
FIG. 9 is a rear view of the lower prosthesis body of FIG. 8.

FIGS. 8 and 9 illustrate side and rear views, respectively, of an alternate embodiment of a lower prosthesis body constructed in accordance with the teachings of the present invention. Lower prosthesis body 300 comprises a tray 305 and stem 310, which in this embodiment are formed in a single unit. However, it should be understood that the present teachings could equally apply to a multi-component prosthesis where the stem and tray form separate components. Desirably, as best seen in FIG. 8, the stem 310 extends downward from the tray 305, forming an angle α relative to the vertical axis—taken relative to the longitudinal axis of the tray 305 (front to rear of the foot). In a preferred embodiment, the angle α will range from 105° to 205°, depending upon the size and orientation of the calcaneus as well as the position of the lower prosthesis body. Moreover, as best seen in FIG. 9, the stem may form an angle β relative to the vertical axis—taken relative to the transverse axis of the tray 305 (medial to lateral side of the foot). In a preferred embodiment, the angle β will range from 155° (on the medial side of the foot) to 240° (on the lateral side of the foot), depending upon the size and orientation of the calcaneus as well as the position of the lower prosthesis body. Desirably, the lower portion of the stem of the implant will not extend outside of the calcaneus. Openings 315 can be provided, if desired, for screws or other attachment means to attach the implant to the talus and/or calcaneus.

The upper surface of the tray can be designed to fit the particular needs and walking requirements anticipated by the physician and patient. For example, a low demand surface, such as for an individual of advanced years having a less-active lifestyle, could comprise a simple smooth arc, without the "peaks and valleys" of the talus that run from anterior to posterior. In addition, a low demand surface may not require a difference in the anterior to posterior talar width, which in an adult male can be approximately 4 to 5 mm wider in its anterior portion than its posterior portion. A higher demand surface, for a more active individual, may incorporate the trochlea (valley) in the talus as well as various other anatomical features found on the talus.

The novel ankle replacement system of the present invention may further comprise an upper prosthesis body. In one embodiment, the upper prosthesis body 170 comprises a tibial stem 150. The tibial stem 150 may be made of any total joint material or materials commonly used in the prosthetic arts, including, but not limited to, metals, ceramics, titanium, titanium alloys, tantalum, chrome cobalt, surgical steel, or any other total joint replacement metal and/or ceramic, bony ingrowth surface, sintered glass, artificial bone, any uncemented metal or ceramic surface, or a combination thereof. The tibial stem 150 may further be covered with one or more coatings such as antimicrobial, antithrombotic, and osteoinductive agents, or a combination thereof. These agents may further be carried in a biodegradable carrier material with which the pores of tibial stem 150 may be impregnated. See U.S. Pat. No. 5,947,893.

The tibial stem 150 may be fixed into the tibia with poly (methylmethacrylate) bone cement, hydroxyapatite, a ground bone composition, screws, or a combination thereof, or any other fixation materials common to one of skill in the art of prosthetic surgery. In the preferred embodiment, the tibial stem 150 is fixed to the tibia with screws 125a and 125b. If screws are used, they can extend anteriorly, posteriorly, medially, laterally and/or at oblique angles, or any combination thereof.

The tibial stem 150 may be variable lengths from 2 cm to 30 cm and variable widths from 6 to 12 mm. In the preferred embodiment, the tibial stem 150 is preferably at least 6 inches in length. Of course, it should be understood that the disclosed tibial stem could be of virtually any length, depending upon the size of the patient, his or her bone dimensions, and the anticipated future mobility of the patient. In general, a larger patient, having larger bones, with a high anticipated mobility (i.e. he or she will be walking/running around quite a bit) would desirably have a longer stem to provide increased stability and broader distribution of stress to prevent subsidence, loosening, and tibial osteolysis. If desired, the stem can incorporate an anti-rotational feature such as outwardly extending fins—for example, one or more fins, 0.5 to 25 cm long, 1 to 3 mm wide, sharp edges or dull, located along the stem—or a bow to the stem—for example, ranging from 1 to 10 degrees bow, anterior or posterior or lateral, or some combination thereof. Moreover, if desired the surface of the tibial stem can incorporate irregularities such as wedges or points, desirably angled towards the knee, which inhibit and/or prevent the tibial stem from subsiding. Alternatively, the width of the tibial stem may vary along the length of the stem, further inhibiting and/or preventing rotation and/or subsidence.

The tip of the tibial stem 150 may additionally have interlocking components, common to those of skill in the art, at its lower surface to allow other components of the upper prosthesis body to lock into the tibial stem. In the preferred embodiment, the tibial stem 150, has a Morse taper 115b at its lower surface.

An upper prosthesis body may be fixed to the tibial stem and/or an interlocking device and/or directly to sections of the tibia. In the preferred embodiment, a concave dome 155, preferably made of a plastic, ceramic, or metal, is attached to the Morse taper 115b. In the preferred embodiment, the upper prosthesis body 170 comprises: a tibial stem 150 made of any total joint material or materials commonly used in the prosthetic arts, including, but not limited to, metals, ceramics, titanium, titanium alloys, tantalum, chrome cobalt, surgical steel, or any other total joint replacement metal and/or ceramic, bony in-growth surface, sintered glass, artificial bone, any uncemented metal or ceramic surface, or a combination thereof, the stem being fixed into the tibia 140 with two screws 125a and 125b; a Morse taper 115b located at the lower surface of the tibial stem 150; and a concave dome 155, preferably made of polyethylene, or another plastic, ceramic or metal, locked into the Morse taper 155b.

In a further embodiment, the upper prosthesis body 170 of the present invention may additionally comprise a fibular prosthesis of any variety known in the art of joint replacement. In still a further embodiment of the present invention, either the lower prosthesis body 95, upper prosthesis body 170, or both, as described above, may be fixed into strengthened or fortified bone. The bones of the subtalar joint, tibia or fibula may be strengthened prior to or during fixation of the prosthesis using the methods described in U.S. Pat. No. 5,827,289, incorporated herein by reference. This type of bone strengthening is particularly suggested for osteoporotic and/or osteopenic patients who wish to have a TAR.

Surgical Procedure

The present invention addresses a novel surgical procedure for performing TAR which reduces healing time and probability of infection, problems which contribute to the failure rate of currently available TARs. The novel surgical procedure comprises introducing some and/or all of an ankle prosthesis for TAR through the tibia and/or small incisions in the foot and/or ankle. The preferred embodiments of the novel surgical procedure described herein will be described as a method to install the preferred embodiment of the TAR system described above. One of skill in the art, however, will note that this type of surgical procedure, i.e. introducing ankle prostheses into the ankle via an exposure in the upper tibia, may be used to introduce some and/or all of any feasible prostheses into the ankle region.

In one embodiment of the novel surgical procedure, an exposure 200 is made at the tibial tubercle with an awl. Once the exposure has been made, the exposure may be kept open under distraction, pulling of the skin, or any other method common in the surgical arts. A surgeon can then introduce various prosthetic parts and surgical instruments through the tibia into the ankle joint. Non-invasive visualization of the procedure can be accomplished through fluoroscopy or real time MRI, as well as through other means well known to those skilled in the art. Alternatively, or in conjunction with such less-invasive means of visualization, open visualization may be used for part and/or all of the procedure.

Figures 6, 6A, 6B:
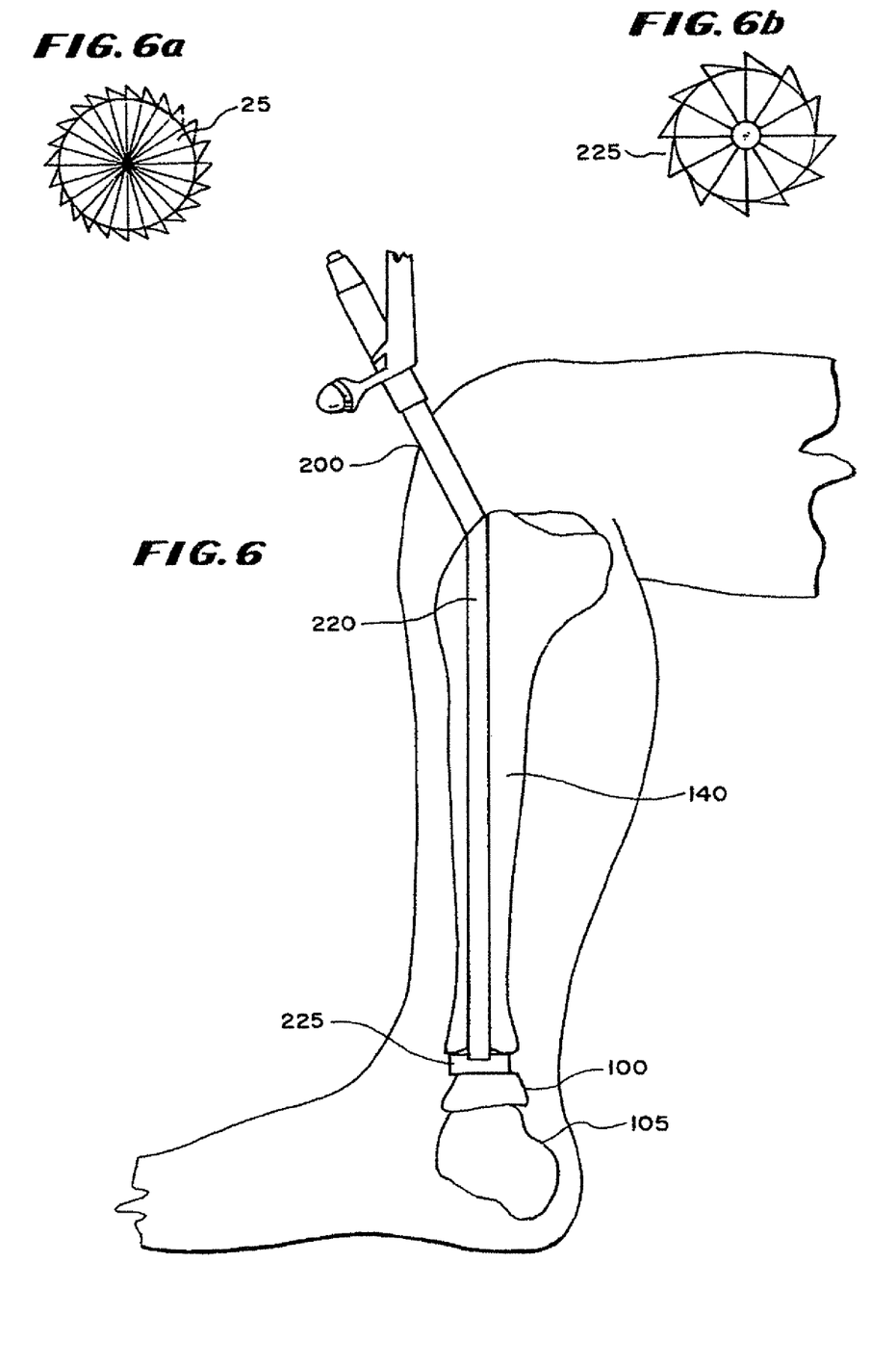
FIG. 6 is a lateral view of the human leg depicting a passed tibial rod adapted to hold an articular reamer.
FIG. 6a is a bottom of an articular reamer.
FIG. 6b is a top view of an articular reamer, showing the attachment member that allows the articular reamer to be attached to the distal end of a tibial reamer.

In the preferred embodiment, a guide wire is placed through the tibia and just through the tibial plafond. A tibial rod 200 with reamers is then pushed down the guide wire. Alternatively, the guide wire and tibial rod may be placed through the tibia simultaneously or a tibial rod may be placed through the tibia without a guide wire. The reamers are preferably 7, 8, 9, or 10 mm wide, depending on the size of the patient's tibia.

In the preferred embodiment, the tibia and tibial plafond are then reamed to create an appropriate cavity in the tibia. Bony cuts may then be made in the talus 100 and the end of the tibia 140 to create a flat surface for prosthetic attachment. Alternatively, it is preferable to ream the top of the talus 100 and the bottom of the tibia 140 with an articular reamer 225 fitted over the end of the tibial rod 220, as depicted in FIG. 6.

Figures 7, 7A, 7B:
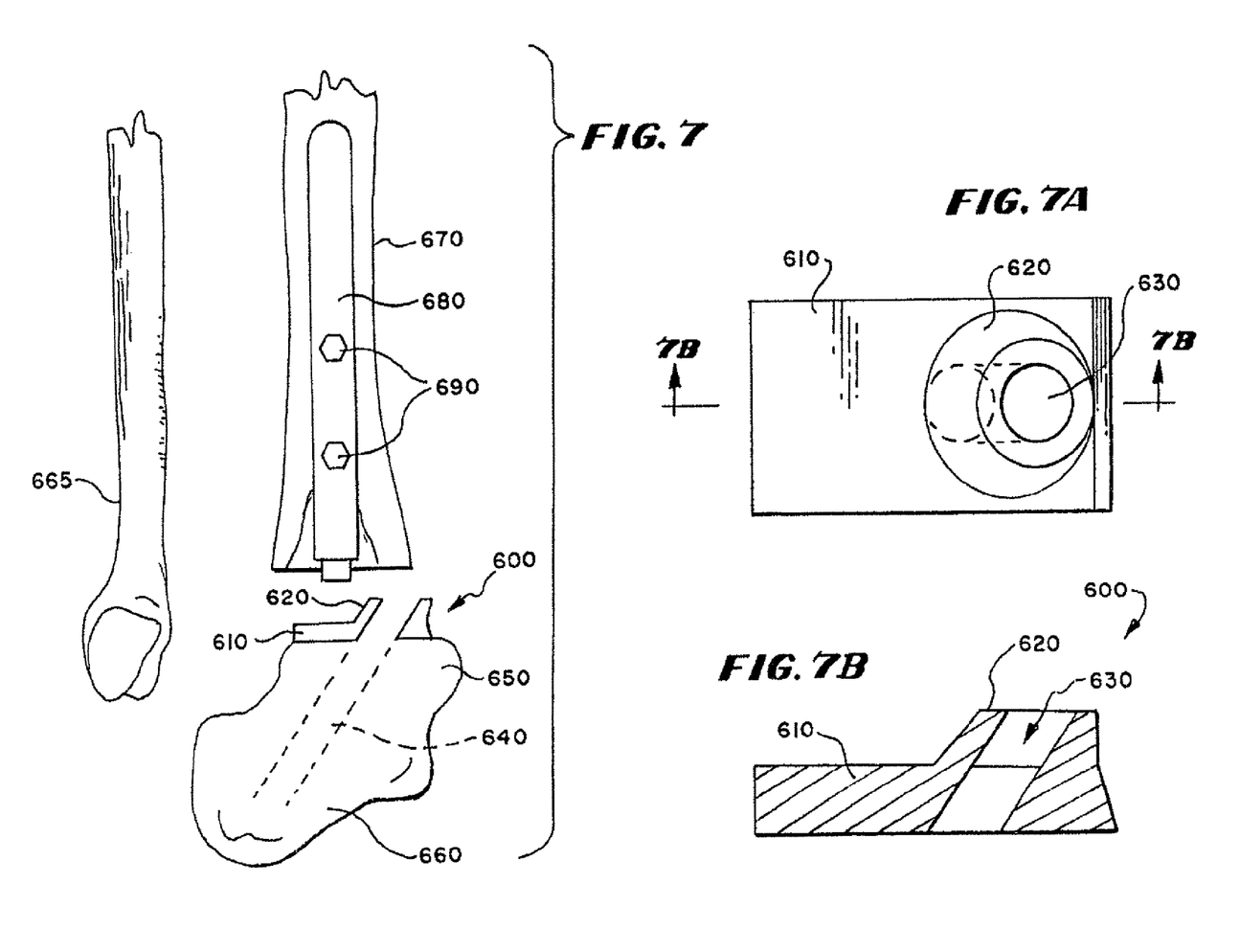
FIG. 7 is a lateral view of the subtalar joint being drilled to form a hole for a bony in-growth stem.
FIG. 7A is a top plan view of the talo-calcaneal jig of FIG. 7.
FIG. 7B is a cross-sectional view of the talo-calcaneal jig of FIG. 7A, taken along lines 7B-7B.

In the preferred embodiment, once the surface of the talus 100 has been flattened, a hole may be drilled through the talus 100 into the posterior section of the calcaneus 105 to form a cavity for insertion of a talo-calcaneal stem 110 as, for example, depicted in FIG. 1 and FIG. 7. Alternatively, the hole may be drilled before the surface of the talus 100 has been flattened. The hole may be drilled using a talar stem jig, or any other surgical equipment used in the surgical arts. The drill bit for the talar stem jig is preferably about 1 mm wider than the width of the talo-calcaneal stem 110.

Once the hole through the talus 100 and calcaneus 105 is drilled to form cavity, any easily accessed cartilage from the talo-calcaneal joint may be scraped. The scraping may be performed with a small angled curet or any other instrument commonly used in the surgical arts. The subtalar joint 90 can then be fused by passing a talo-calcaneal stem 110 down the cavity. In one embodiment, the cavity may be partially filled with a bone cement prior to the installation of the talo-calcaneal stem 110 to help fix the talo-calcaneal stem 110 to the subtalar joint 90. In the preferred embodiment, the stem 110 has a bore hole to allow further anchoring of the stem with a screw as described below.

The talo-calcaneal stem 110 preferably comprises a Morse taper 115*a* at its upper surface. In the preferred embodiment, once the talo-calcaneal stem 110 is installed into the cavity, a tray 130, and a plastic 5 convex dome, preferably made of polyethylene, are placed over and locked into the Morse taper 115*a*. In the preferred embodiment, the tray 130 and overhang portion 131 of the tray are then anchored or fixed to the subtalar joint 90. Preferably the tray 130 and overhang 131 are anchored to the subtalar joint 90 with screws 133*a* and 133*b* such that screw 133*a* also passes through the talo-calcaneal stem 110, as best seen in FIG. 4, to provide additional anchoring for the talo-calcaneal stem 110.

After the lower prosthesis body 95 of the present invention has been installed, or alternatively, while the lower prosthesis body 95 is being installed or before the lower prosthesis body 95 is installed, an upper prosthesis body 170 may also be installed. In the preferred embodiment, a concave dome 155, preferably made of polyethylene, is placed into the ankle joint. A tibial stem 150 is then passed down the tibia to the ankle joint. The tibial stem 150 is preferably approximately 1 mm less in diameter than the size of the largest reamer, and preferably comprises a Morse taper 115*b* at its lower surface.

Once the tibial stem 150 is installed, the concave dome 155 can be locked into Morse taper 115*b*. The tibial stem 150 may be fixed into the tibia with bone cement, screws, nails, anchors, or a combination thereof. In the preferred embodiment, the tibial stem 150 is fixed into the tibia with screws 125*a* and 125*b*. Once the lower prosthesis body 95, upper prosthesis body 170, or both, have been installed, any remaining surgical instruments may be removed through the exposure 200 and the exposure may be sutured closed.

In a further alternative embodiment, a cavity can be formed in the calcaneus using the teachings of U.S. Pat. No. 5,827,289 to Reiley, either before, during, or after access to the calcaneus has been accomplished through the tibia. This cavity can eventually be filled with material which hardens around some or all of the prosthesis, thereby anchoring the lower prosthesis primarily into the calcaneus. If desired, the prosthesis could incorporate a plurality of rotatable and/or slidable joints, which can allow transverse motion between the talus and the calcaneus while concurrently allowing relative motion between the talus and the tibia, thereby more accurately mimicking the natural motion of the human foot.

In other embodiments, the upper prosthesis body 170 of the present invention may additionally comprise a fibular prosthesis of any variety known in the art of joint replacement, which may also be installed through exposure 200. In still further embodiments of the present invention, either the lower prosthesis body 95, upper prosthesis body 170, or both, as described above, may be fixed into strengthened or fortified bone. The bones of the subtalar joint, tibia or fibula may be strengthened prior to or during fixation of the prosthesis using the methods described in U.S. Pat. No. 5,827,289 to Reiley. This type of bone strengthening procedure is particularly suggested for osteoporotic patients who wish to have a TAR.

Surgical Instruments

One novel surgical instrument particularly well suited for use with the devices and methods of the present invention is a telescoping reamer which significantly simplifies the preparation of the ankle joint for receiving the prosthesis and greatly reduces the amount of trauma experience by the tissues at the ankle joint. Desirably, the reamer will comprise a cylindrical shaft having a maximum diameter less than the reamed inner diameter of the tibia, and a length equal to or greater than the length of the tibia. At the distal end of the reamer, a reamer fitting, preferably a snap lock or other type of quick-release fitting, may be formed. At the proximal end of the reamer, a drive handle or other device is desirably fitted to provide torsional and axial forces to the reamer.

Desirably, a reamer head can be attached to the distal end of the reamer. If the reamer head is of a smaller maximum diameter than the inner diameter of the reamed tibia, the reamer head can be passed down through the tibia and/or calcaneus, and the lower surfaces of the tibia, for the prosthesis. However, if the reamer head is of equal or greater diameter than the inner diameter of the reamed tibia, the reamer head can be alternatively inserted into the joint region through an incision made at or near the joint, and can be attached to the distal end of the reamer which extends through the tibia. In this manner, the reamer head can be inserted through a very small incision, such as a vertically extending incision, but can be properly positioned and operated at the end of the reamer. When reaming is completed, the reamer head can be detached and removed through the same small incision, and the reamer withdrawn through the reamed tibia.

In a similar manner, the prosthesis could be inserted through the reamed tibia, or could alternatively be inserted through one or more smaller incisions through the ankle and/or foot, and then manipulated using instruments and/or visualization devices passing through the reamed tibia. In fact, if desired, the prosthesis could be formed of a series of smaller components which are ultimately assembled within the joint cavity.

Another novel surgical instrument for use with the devices and methods of the present invention is a talo-calcaneal jig 600, best shown in FIGS. 7, 7A and 7B. FIG. 7 depicts a tibia 670 which is slightly distracted from a fibula 665, a talus 650 and a calcaneus 660 of a human ankle. A tibial stem 680 extends through at least a portion of the tibia 670, and is secured to the tibia by screws 690. The fibula 665 is distracted from the tibia 670 and the talus 650 and calcaneus 660. A jig 600 is positioned on top of the talus 650. The jig 600 desirably comprises a base plate 610 and extension piece 620, with a passage 630 extending therethrough. The passage 630 is desirably sized to accommodate a drill (not shown) for creating a void 640 within the talus 650 and calcaneus 660 for implantation of the prosthesis. Desirably, the jig 600 will fit over the upper surface of the talus, and will guide the drill (not shown) in creating a void 640 of desired shape and size into the talus 650 and calcaneus 660. Once the void is created, the jig 600 can be removed and the prosthesis (not shown) inserted into the void 640.

It should be understood that the devices and methods of the present invention could be used as an index (initial) total ankle replacement, as well as a revision ankle replacement. If used as a revision device, only a portion of the disclosed methods and devices may be necessary in conjunction with such a procedure.

Other embodiments and uses of the inventions described herein will be apparent to those skilled in the art from consideration of the specification and practice of the inventions disclosed. All documents referenced herein are specifically and entirely incorporated by reference. The specification should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

I claim:

1. A method for reconstructing an ankle having a talus, a caleaneus, and a subtalar joint between the talus and calcaneus, said method comprising:
    providing a prosthesis body including a stem having an upper end and a lower end;
    forming a cavity from the top of said talus to a distal portion of said calcaneus; and
    inserting the stem into the cavity such that the stem extends through the subtalar joint so as to allow fixation of the stem to both the talus and calcaneus.

2. The method of claim 1, further comprising;
    making a bony cut to an upper portion of the talus to create flat surface; and
    attaching a tray to the flat surface of the talus, the tray including an overhang portion sized and configured to extend outward of the talus and overlap a portion of the calcaneus.

* * * * *